United States Patent
Yen et al.

(10) Patent No.: US 10,745,433 B2
(45) Date of Patent: Aug. 18, 2020

(54) COMPOUNDS FOR INHIBITING CANCER AND VIRUS

(71) Applicant: Taipei Medical University, Taipei (TW)

(72) Inventors: Yun Yen, Arcadia, CA (US); Jing-Ping Liou, Taipei (TW); Yun-Ru Liu, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 16/069,100

(22) PCT Filed: Jan. 12, 2017

(86) PCT No.: PCT/US2017/013253
§ 371 (c)(1),
(2) Date: Jul. 10, 2018

(87) PCT Pub. No.: WO2017/123809
PCT Pub. Date: Jul. 20, 2017

(65) Prior Publication Data
US 2019/0016743 A1    Jan. 17, 2019

Related U.S. Application Data

(60) Provisional application No. 62/277,653, filed on Jan. 12, 2016.

(51) Int. Cl.
*C07H 15/203*    (2006.01)
*A61K 31/7034*    (2006.01)
(Continued)

(52) U.S. Cl.
CPC ......... *C07H 15/203* (2013.01); *A61K 31/166* (2013.01); *A61K 31/216* (2013.01);
(Continued)

(58) Field of Classification Search
CPC combination set(s) only.
See application file for complete search history.

(56) References Cited

U.S. PATENT DOCUMENTS 7,626,042 B2 * 12/2009 Muto .................. C07D 209/48
544/172
2007/0123493 A1    5/2007 Koyano et al.
(Continued)

FOREIGN PATENT DOCUMENTS

CN    103130696 A    6/2013
DE         150471 A1    9/1981
(Continued)

OTHER PUBLICATIONS

Berge, S. M., Bighiey, L. D., & Monkhouse, D. C. (1977). Pharmaceutical salts. journal of pharmaceutical sciences, 66(1), 1-19.
International Search Report in International Patent Application No. PCT/US2017/013253, dated Apr. 24, 2017 in 15 pages.
Xu, Miao, et al. "Identification of small-molecule inhibitors of Zika virus infection and induced neural cell death via a drug repurposing screen." Nature medicine 22.10 (2016): 1101, pp. 1-10; published online Aug. 29, 2016; doi:101038/nm.4184.
(Continued)

*Primary Examiner* — San Ming R Hui
(74) *Attorney, Agent, or Firm* — Duane Morris LLP

(57) ABSTRACT

The invention relates to compounds for inhibiting a cancer cell or a virus. Particularly, the invention provides compounds for inhibiting, treating and/or preventing cancer and Zika virus.

13 Claims, 7 Drawing Sheets

(51) Int. Cl.
*C07C 235/64* (2006.01)
*C07D 211/58* (2006.01)
*A61K 31/4409* (2006.01)
*A61K 31/381* (2006.01)
*A61K 45/06* (2006.01)
*A61P 35/00* (2006.01)
*A61K 31/222* (2006.01)
*A61K 31/166* (2006.01)
*A61K 31/216* (2006.01)
*A61K 31/4545* (2006.01)

(52) U.S. Cl.
CPC .......... *A61K 31/222* (2013.01); *A61K 31/381* (2013.01); *A61K 31/4409* (2013.01); *A61K 31/4545* (2013.01); *A61K 31/7034* (2013.01); *A61K 45/06* (2013.01); *A61P 35/00* (2018.01); *C07C 235/64* (2013.01); *C07D 211/58* (2013.01)

(56) References Cited

U.S. PATENT DOCUMENTS

| | | |
|---|---|---|
| 2008/0161324 A1 | 7/2008 | Johansen et al. |
| 2014/0294957 A1 | 10/2014 | Stein |
| 2015/0174086 A1 | 6/2015 | Scheffler |
| 2015/0361031 A1 | 12/2015 | Zhou et al. |

FOREIGN PATENT DOCUMENTS

| | | |
|---|---|---|
| WO | 2001/074835 A1 | 10/2001 |
| WO | 2010101648 A1 | 9/2010 |
| WO | 2014/113467 A1 | 7/2014 |

OTHER PUBLICATIONS

Extended European Search Report in EP Application No. 17738972.3, dated Oct. 10, 2019, in 6 pages.

\* cited by examiner

COMPOUNDS FOR INHIBITING CANCER AND VIRUS

CROSS-REFERENCE TO RELATED APPLICATIONS

This application is a § 371 national stage entry of International Application No. PCT/US2017/013253, filed Jan. 12, 2017, which claims priority to U.S. Provisional Patent Application No. 62/277,653 filed Jan. 12, 2016, the entire contents of which are incorporated herein by reference.

FIELD OF THE INVENTION

The invention relates to compounds for inhibiting a cancer cell or a virus. Particularly, the invention provides compounds for inhibiting, treating and/or preventing cancer and Zika virus.

BACKGROUND OF THE INVENTION

Cancer is a significant health problem throughout the world and is still among the leading causes of death. Cancer is a group of diseases characterized by dysregulation of cell differentiation and proliferation; in advanced stages, it spreads to other areas of the body including vital organs and bone. Although tremendous advances have been made in the availability of multiple therapeutic regimens to treat cancer, currently available chemotherapy still remains unsatisfactory, and the prognosis for the majority of patients diagnosed with cancer remains dismal. Furthermore, many patients do not respond to any treatments. Of those that do respond to standard therapies, the effect is usually short-lived as resistance develops to the initial therapeutic regimens.

Niclosamide, sold under the trade name Niclocide among others, is a medication used to treat tapeworm infestations. However, niclosamide has high toxicity and significant side effects, so the compound cannot be administered in higher dose or higher frequency. U.S. 20140294957 discloses that niclosamide and derivatives thereof effectively inhibit transcription of the S100A4 gene, resulting in inhibition and/or reduction of S100A4-induced cell motility, invasiveness, metastasis and proliferation of human cancer cells. U.S. 20150174086 relates to therapeutic uses of niclosamide for the treatment of cancer.

ZIKV, a mosquito-borne flavivirus, is a global health concern and rapid progress has been made to understand its pathogenesis and to develop human in vitro models and animal in vivo models. A reference provides in vitro data suggesting the use of niclosamide in the inhibition of Zika virus infection (Nature Medicine, published online 29 Aug. 2016; doi:10.1038/nm.4184). However, there is currently no drug approved to treat or prevent Zika virus infection.

SUMMARY OF THE INVENTION

The invention provides a series of prodrugs of niclosamide and their superior efficacy in inhibition, prevention and/or treatment of a cancer or Zika virus infection.

The invention provides a compound having the following Formula (I),

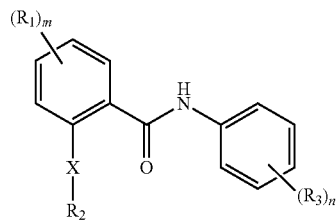

wherein
X is O, N or S;
m is an integer of 1 to 4;
n is an integer of 1 to 5;
$R_1$ is halogen, $NH_2$, $NO_2$, OH, $C_{1-10}$alkyl, $C_{2-10}$alkenyl, $C_{2-10}$alkynyl, $C_{1-10}$alkyloxy or $C_{1-10}$alkylthio;
$R_2$ is furanosyl, pyranosyl, —$C_{1-10}$alkyloxy-C(O)$C_{1-10}$alkyl or $COR_4$, wherein $R_4$ is a 5- or 6-membered saturated or unsaturated heterocyclic ring containing 1 or 2 heteroatom selected from N, O and S, wherein the heterocyclic ring is unsubstituted or substituted with a 5- or 6-membered saturated heterocyclic ring containing 1 or 2 heteroatom selected from N, O and S; and
$R_3$ is halogen, $NH_2$, $NO_2$, OH, halo$C_{1-10}$alkyl, $C_{1-10}$alkyl, $C_{2-10}$alkenyl, $C_{2-10}$alkynyl, $C_{1-10}$alkyloxy or $C_{1-10}$alkylthio;
or a tautomer, stereoisomer or enantiomer thereof, or a solvate or a pharmaceutically acceptable salt thereof.

The invention provides a pharmaceutical composition comprising a compound of Formula (I) of the invention.

The invention also provides a method for inhibiting tumor growth in a subject, comprising administering to the subject a therapeutically effective amount of the compound of Formula (I) of the invention. Also provided is a method for treating or preventing a disease associated with embryonic development, cell proliferation, cell differentiation, cell-fate decisions, cell migration or maintenance of tissue homeostasis, regeneration or plasticity, comprising administering to a subject an effective amount of the compound of Formula (I) of the invention.

The invention further provides a method for inhibiting Zika virus, comprising contacting a compound of the invention with the Zika virus.

The invention further provides a method for treating and/or preventing Zika virus infection, comprising administrating an effective amount of a compound of the invention to a subject.

DETAILED DESCRIPTION OF THE INVENTION

Figure 1A:
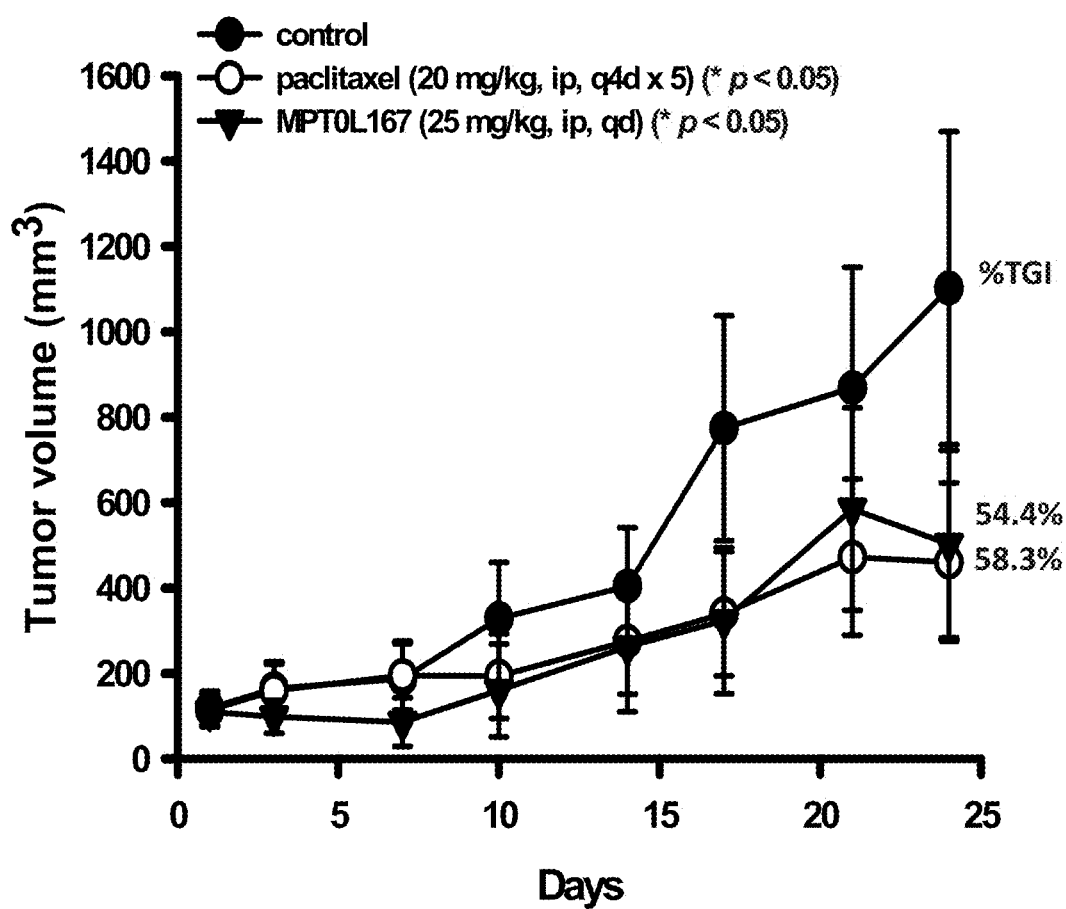
FIGS. 1(A) and (B) show that anti-cancer activity of MPT0L167 in human breast MDA-MB-231 xenograft model. (A), MPT0L167 reduces tumor volume. (B), MPT0L167 does not significantly reduce body weight.

The invention is based on, at least in part, a potential therapeutic target in human cancer. On the other hand, the compounds of the invention can be used as anti-Zika viral agent.

Terms not specifically defined herein should be understood according to the meanings that would be given to them by one of skill in the art in light of the disclosure and the context. As used in the specification, however, unless specified to the contrary, the following terms have the meaning indicated according to the following conventions.

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl The terms "a" and "an" refer to one or more.

The terms "disease" and "disorder" herein can be used interchangeably.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compounds, compositions and methods of the present invention may be used for instance as therapeutic treatment over a period of time as well as for chronic therapy. In addition, the terms "treatment" and "treating" comprise prophylactic treatment, i.e. a treatment of patients at risk to develop a condition mentioned hereinbefore, thus reducing said risk.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The term "substituted" as used herein means that any one or more hydrogens on the designated atom, radical or moiety are replaced with a selection from the indicated group, provided that the atom's normal valence is not exceeded, and that the substitution results in an acceptably stable compound.

The term "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active, wherein the enantiomer rotates the plane of polarized light in one direction and its mirror image compound rotates the plane of polarized light in the opposite direction.

The term "racemic" refers to a mixture of equal parts of enantiomers that is optically inactive.

The term "resolution" refers to the separation or concentration or depletion of one of the two enantiomeric forms of a molecule.

The term "alkyl," as used herein, alone or in combination, refers to a straight-chain or branched-chain alkyl radical containing from 1 to 10 carbon atoms. In further embodiments, said alkyl will comprise from 1 to 8, 1 to 6 or 1 to 4 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

As used herein, the term "alkenyl" refers to straight or branched chain hydrocarbon chains containing the specified number of carbon atoms and one or more double bonds. For example, "$C_2$-$C_6$ alkenyl" is selected from straight chain and branched non-cyclic hydrocarbons having from 2 to 6 carbon atoms and including at least one carbon-carbon double bond. Representative straight chain and branched $C_2$-$C_6$ alkenyl groups include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, and 3-hexenyl.

As used herein, the term "alkynyl" refers to straight or branched chain hydrocarbon chains containing the specified number of carbon atoms and one or more triple bonds. For example, "$C_2$-$C_6$ alkynyl" is selected from straight chain and branched non-cyclic hydrocarbon having from 2 to 6 carbon atoms and including at least one carbon-carbon triple bond. Representative straight chain and branched $C_2$-$C_6$ alkynyl groups include -acetylenyl, -propynyl, -1-butyryl, -2-butyryl, -1-pentynyl, -2-pentynyl, -3-methyl-1-butynyl, -4-pentynyl, -1-hexynyl, -2-hexynyl, and -5-hexynyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. The point of attachment may be on the oxygen or carbon atom.

As used herein, the term "alkylthio" (also termed alkylsulfanyl) refers to straight-chain or branched alkyl groups (preferably having 1 to 6 carbon atoms, e.g. 1 to 4 carbon atoms ($C_1$-$C_6$-alkylthio), which are bound to the remainder of the molecule via a sulfur atom at any bond in the alkyl group. Examples of $C_1$-$C_4$-alkylthio include methylthio, ethylthio, n-propylthio, isopropylthio, n-butylthio, sec-butylthio, isobutylthio and tert-butylthio. Examples of $C_1$-$C_6$-alkylthio include, apart from those mentioned for $C_1$-$C_4$-alkylthio, 1-, 2- and 3-pentylthio, 1-, 2- and 3-hexylthio and the positional isomers thereof.

As used herein, the term "saturated" includes substituents saturated with hydrogens.

As used herein, the term "5- or 6-membered saturated heterocyclic ring containing 1 or 2 heteroatoms", wherein those heteroatom(s) are selected from N, O or S and are ring members, refers to monocyclic radicals, the monocyclic radicals being saturated. The heterocyclic radical may be attached to the remainder of the molecule via a carbon ring member or via a nitrogen ring member. Examples of the "5- or 6-membered saturated heterocyclic ring containing 1 or 2 heteroatoms include, but are limited to, imidazolidinyl, oxazolidinyl, thiazolidinyl, pyrrolidinyl, oxolanyl, thiolanyl, piperidinyl, piperazinyl, morpholinyl, oxanyl and thianyl.

As used herein, the term "5- or 6-membered unsaturated heterocyclic ring containing 1 or 2 heteroatoms", wherein those heteroatom(s) are selected from N, O or S and are ring members, refers to monocyclic radicals, the monocyclic radicals being unsaturated. The heterocyclic radical may be attached to the remainder of the molecule via a carbon ring member or via a nitrogen ring member. Examples of the "5- or 6-membered unsaturated heterocyclic ring containing 1 or 2 heteroatoms include, but are limited to, pyrrolyl, furanyl, thienyl, pyridinyl, pyranyl, thiopyranyl, oxazinyl and thiazinyl.

In one aspect, the invention provides a compound having the following Formula (I),

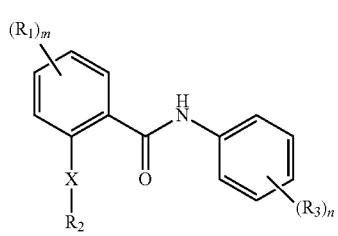

wherein
X is O, N or S;
m is an integer of 1 to 4;
n is an integer of 1 to 5;
$R_1$ is halogen, $NH_2$, $NO_2$, OH, $C_{1-10}$alkyl, $C_{2-10}$alkenyl, $C_{2-10}$alkynyl, $C_{1-10}$alkyloxy or $C_{1-10}$alkylthio;
$R_2$ is furanosyl, pyranosyl, —$C_{1-10}$alkyloxy-C(O)$C_{1-10}$alkyl or $COR_4$, wherein $R_4$ is a 5- or 6-membered saturated or unsaturated heterocyclic ring containing 1 or 2 heteroatom selected from N, O and S, wherein the heterocyclic ring is unsubstituted or substituted with a 5- or 6-membered saturated heterocyclic ring containing 1 or 2 heteroatom selected from N, O and S; and
$R_3$ is halogen, $NH_2$, $NO_2$, OH, halo$C_{1-10}$alkyl, $C_{1-10}$alkyl, $C_{2-10}$alkenyl, $C_{2-10}$alkynyl, $C_{1-10}$alkyloxy or $C_{1-10}$alkylthio;
or a tautomer, stereoisomer or enantiomer thereof, or a solvate or a pharmaceutically acceptable salt thereof.

In some embodiments, X is O.
In some embodiments, m is 1.
In some embodiments, n is 2.
In some embodiments, $R_1$ is halogen or $C_{1-10}$alkyl. Preferably, $R_1$ is F, Cl, Br or C1-4alkyl. More preferably, $R_1$ is Cl.

In some embodiments, $R_2$ is arabinopyranosyl, glucopyranosyl, galactopyranosyl, xylopyranosyl, arabinopyranosyl, ribopyranosyl, lyxopyranosyl, ribulopyranosyl, allopyranosyl, altropyranosyl, mannopyranosyl, idopyranosyl, arabinofuranosyl, glucofuranosyl, galactofuranosyl, xylofuranosyl, arabinofuranosyl, ribofuranosyl, lyxofuranosyl, ribulofuranosyl, allofuranosyl, altrofuranosyl, mannofuranosyl, idofuranosyl, C(O)pyridinyl, C(O)thienyl, —$C_{1-4}$alkyloxy-C(O)$C_{1-4}$alkyl, or —C(O)bipiperidinyl. Preferably, $R_2$ is glucopyranosyl, 1,4'-bipiperidinyl, C(O)pyridinyl or —$CH_2OC(O)CH_3$.

In some embodiments, $R_3$ is $CF_3$, F, Cl, Br or $NO_2$. Preferably, $R_3$ is $CF_3$, Cl or $NO_2$.

In some embodiments, the compound of Formula (I) is selected from the group consisting of:

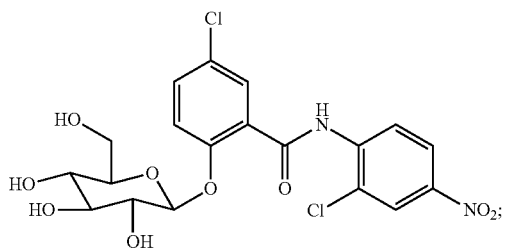
(MPT0L167)

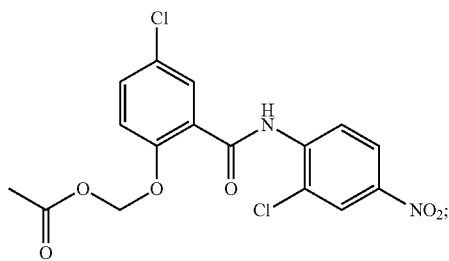
(MPT0L180)

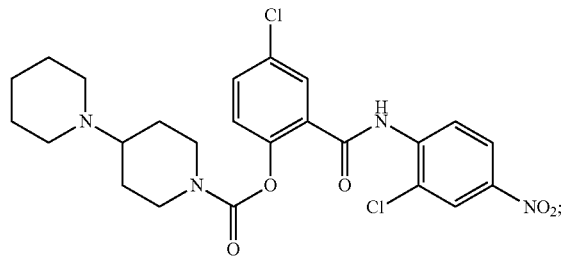
(MPT0L196)

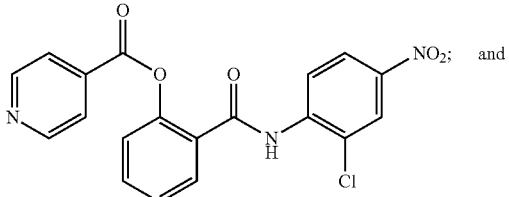

and

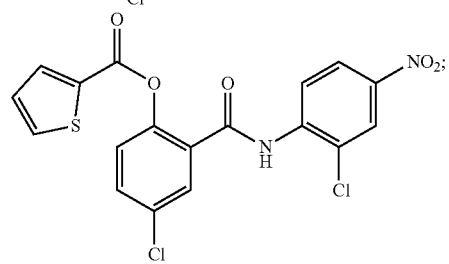

or a tautomer, stereoisomer or enantiomer thereof, or a solvate or a pharmaceutically acceptable salt thereof.

The invention disclosed herein also encompasses pharmaceutically acceptable salts of the disclosed compounds. In one embodiment, the present invention includes any and all non-toxic, pharmaceutically acceptable salts of the disclosed compounds, comprising inorganic and organic acid addition salts and basic salts. The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (See Pharmaceutical salts, Birge, S. M. et al., J. Pharm. Sci., (1977), 66, 1-19.)

The invention disclosed herein also encompasses solvates of the disclosed compounds. One type of solvate is a hydrate. Solvates typically do not contribute significantly to the physiological activity or toxicity of the compounds and as such can function as pharmacological equivalents.

The invention disclosed herein also encompasses tautomers and isomers of the disclosed compounds. A given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as, for instance, hydrates including solvates of the free compounds or solvates of a salt of the compound.

The compounds of the present invention can be prepared using methods known to those skilled in the art in view of this disclosure. For example, the preferred compounds of the invention can be prepared as shown in the following schemes.

Scheme 1 describes the synthesis of a series of the compounds of the invention (2-4). The commercially available compound 1 was reacted with 2,3,4,6-tetra-O-acetyl-α-D-glucopyranosyl bromide in the presence of TBAB and DIPEA, and was subject to the deprotection of acetyl groups carried out by Amberlite® under basic conditions to afford the glycoside 2. The reaction of compound 1 with bromomethyl acetate in the presence of K$_2$CO$_3$ provided compound 3. To attach the same side chain with irinotecan, compound 1 was reacted with 1-chlorocarbonyl 4-piperidinopiperidine, yielding compound 4. Finally, compound 1 was reacted with DMF in the presence of CuCl, 70% t-BuOOH to afford compound 4.

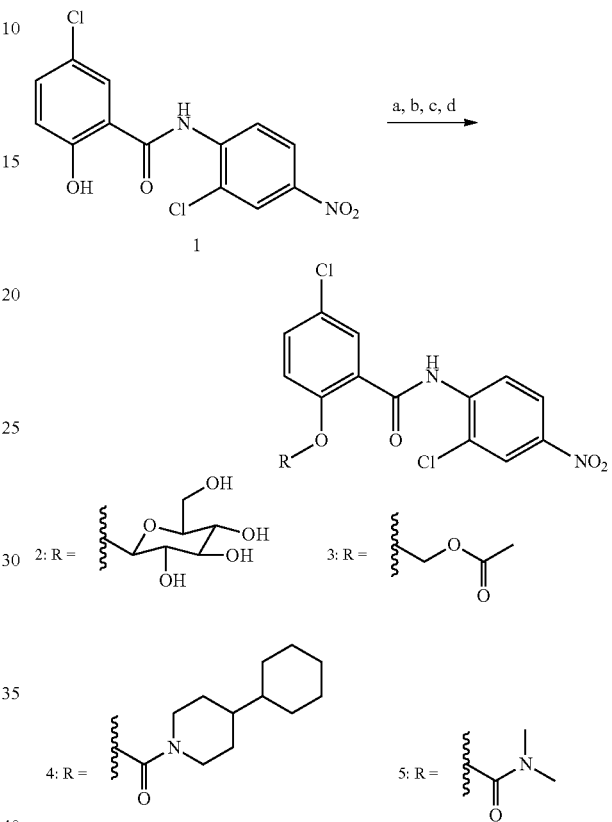

Scheme 1. Synthesis of Compounds 32-35.

Reagents and conditions: For 32: (a) i. 2,3,4,6-tetra-O-acetyl-α-D-glucopyranosyl bromide, TBAB, DIPEA, DCM, 60° C.; ii. K$_2$CO$_3$, Amberlite® IR-120 hydrogen form, 9%. For 33: (b) bromomethyl acetate, K$_2$CO$_3$, ACN, rt, 86%. For 34: (c) 1-chlorocarbonyl 4-piperidinopiperidine, DMAP, pyridine, 80° C., 14%. For 35: (d) CuCl, 70% t-BuOOH, DMF, 70° C., 15%.

The following schemes show the synthesis of other compounds of the invention.

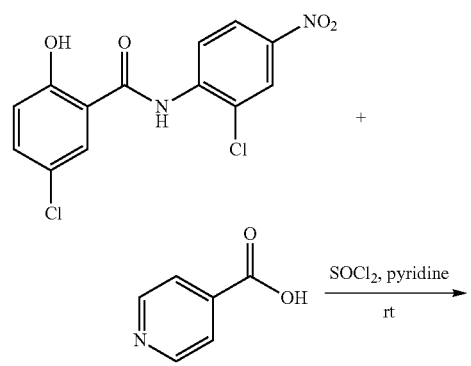

-continued

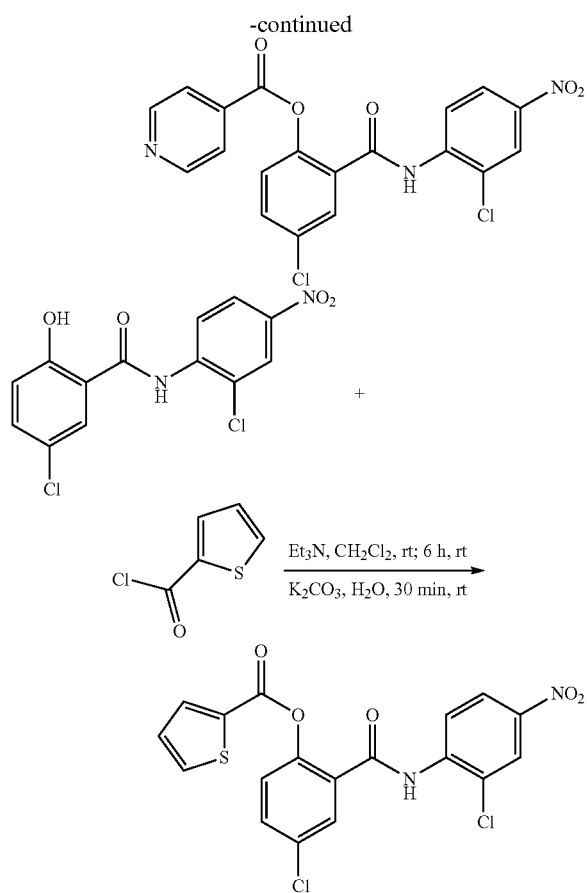

In one aspect, the invention provides a pharmaceutical composition comprising a compound of Formula (I) of the invention.

In an another further aspect, the invention provides a method for inhibiting tumor growth in a subject, comprising administering to the subject a therapeutically effective amount of the compound of Formula (I) of the invention.

In an another further aspect, the invention provides a method for treating or preventing a disease associated with embryonic development, cell proliferation, cell differentiation, cell-fate decisions, cell migration or maintenance of tissue homeostasis, regeneration or plasticity, comprising administering to a subject an effective amount of the compound of Formula (I) of the invention.

Such method includes administering a compound of the present invention to a subject in an amount sufficient to treat the condition. Preferably, the disease is cancer. For example, the cancers include but are not limited to the group consisting of: neuroblastoma; lung cancer; bile duct cancer; non small cell lung carcinoma; hepatocellular carcinoma; head and neck squamous cell carcinoma; squamous cell cervical carcinoma; lymphoma; nasopharyngeal carcinoma; gastric cancer; colon cancer; uterine cervical carcinoma; gall bladder cancer; prostate cancer; breast cancer; testicular germ cell tumors; colorectal cancer; glioma; thyroid cancer; basal cell carcinoma; gastrointestinal stromal cancer; hepatoblastoma; endometrial cancer; ovarian cancer; pancreatic cancer; renal cell cancer, Kaposi's sarcoma, chronic leukemia, sarcoma, rectal cancer, throat cancer, melanoma, colon cancer, bladder cancer, mastocytoma, mammary carcinoma, mammary adenocarcinoma, pharyngeal squamous cell carcinoma, testicular cancer, gastrointestinal cancer, or stomach cancer and urothelial cancer. In one embodiment, the applicable dose range of the compound of the invention is usually from about 1 mg/kg to about 15 mg/kg body weight; preferably, about 1 mg/kg to about 12 mg/kg, about 1 mg/kg to about 10 mg/kg, about 1 mg/kg to about 8 mg/kg, about 1 mg/kg to about 5 mg/kg, about 2 mg/kg to about 15 mg/kg, about 2 mg/kg to about 12 mg/kg, about 2 mg/kg to about 10 mg/kg, about 2 mg/kg to about 8 mg/kg, about 2 mg/kg to about 5 mg/kg, about 2.5 mg/kg to about 15 mg/kg, about 2.5 mg/kg to about 12 mg/kg, about 2 mg/kg to about 10 mg/kg, about 2 mg/kg to about 8 mg/kg, about 3 mg/kg to about 15 mg/kg, about 3 mg/kg to about 12 mg/kg, about 3 mg/kg to about 10 mg/kg, about 3 mg/kg to about 8 mg/kg, about 5 mg/kg to about 15 mg/kg, about 5 mg/kg to about 12 mg/kg or about 5 mg/kg to about 8 mg/kg. In one embodiment, the dose range of the compound of the invention applicable is about 2.5 mg/kg to about 12 mg/kg.

In another aspect, the invention provides a method for inhibiting Zika virus, comprising contacting a compound of the invention with the Zikv virus.

In another aspect, the invention provides a method for treating and/or preventing Zika virus infection, comprising administrating an effective amount of a compound of the invention to a subject.

The invention surprisingly found that the compounds of the invention significantly inhibit Zika virus in vivo with low toxicity and thus can be used as anti-Zika virus agents to treat and/or prevent Zika virus infection. The compounds of the invention have longer half-life than niclosamide, so the compound of the invention has a superior in vivo effect in inhibiting Zika virus infection to niclosamide.

The compound of the present invention may be administered to a mammal in the form of a raw chemical without any other components present. The compound is preferably administered as part of a pharmaceutical composition containing the compound combined with a suitable pharmaceutically acceptable carrier. Such a carrier can be selected from pharmaceutically acceptable excipients, diluents and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g. a human, orally at a therapeutically effective dose, or an equivalent amount of a pharmaceutically acceptable salt, prodrug or solvate thereof, per day to treat, prevent or ameliorate the particular disorder. A useful oral dose of a compound of the present invention administered to a mammal is from about 5 to about 100 mg per kg body weight of the mammal, or an equivalent amount of the pharmaceutically acceptable salt, prodrug or solvate thereof. For intramuscular injection, the dose is typically about one-half of the oral dose.

The compounds of the present invention may be useful in combination with one or more second therapeutic agents, particularly therapeutic agents suitable for the treatment and/or prevention of the conditions and diseases presented previously.

For example in cancer treatment and/or prevention, it will be appreciated that the combination of a FZD-binding agent and a second therapeutic agent may be administered in any order or concurrently. In one embodiment, the FZD-binding agents will be administered to patients that have previously undergone treatment with the second therapeutic agent. In other embodiments, the FZD-binding agent and the second therapeutic agent will be administered substantially simultaneously or concurrently. The second therapeutic agent includes, but is not limited to, a mitotic inhibitor (such as a taxane (preferably paclitaxel or docetaxel), vinca alkaloid (preferably, vinblastine, vincristine, vindesine or vinorelbine) or vepesid; an anthracycline antibiotic (such as doxorubicin, daunorubicin, daunorubicin, epirubicin, idarubicin, valrubicin or mitoxantrone); a nucleoside analog (such as gemcitabine); an EGFR inhibitor (such as gefitinib or erlotinib); a folate antimetabolite (such as trimethoprim, pyrimethamine or pemetrexed); cisplatin or carboplatin. Examples of the second therapeutic agent include but are not limited to tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel and vincristine, and derivatives and prodrugs thereof.

For example in anti-Zika virus treatment and/or prevention, the compound or the pharmaceutical composition comprising the compound of the invention can be administered independently or in combination with another anti-viral agent. The dose range of the compound of the invention applicable is as described herein. In one embodiment, the compound of the invention can be administered once daily in the treatment of Zika virus infection.

Pharmaceutically acceptable carriers and diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of the invention, diluents, dispersing and surface active agents, binders, and lubricants. One skilled in this art may further formulate the compound of the invention in an appropriate manner, and in accordance with accepted practices, such as those disclosed in Remington's Pharmaceutical Sciences, Gennaro, Ed., Mack Publishing Co., Easton, Pa. 1990.

The actual therapeutically effective amount or therapeutic dosage will of course depend on factors known by those skilled in the art such as age and weight of the patient, route of administration and severity of disease. In any case, the combination will be administered at dosages and in a manner which allow a therapeutically effective amount to be delivered based upon subject's unique condition.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

Biological Assay
Growth Inhibition Assay

The compounds of the invention were subjected to growth inhibition assay. Cells were seeded in 96-well plastic plates and exposed to the compounds of the invention for 72 hours. Cell viability was assessed using the 3-(4,5-dimethylthiazol-2-yl)-2,5-diphenyltetrazolium bromide assay. The $IC_{50}$ results are shown in the table below; #166 is niclosamide; MPT0L167, MPT0L180 and MPT0L196 are Compound 32, Compound 33 and Compound 34 mentioned in Examples 1 to 3 below, respectively; and MPT0L175 is the glucose-acetyl derivative of #67.

| Cell line | Type | #166 | MPT0L167 | MPT0L175 | MPT0L180 | MPT0L196 |
|---|---|---|---|---|---|---|
| DU145 | Prostate cancer | >10 | >25 | >25 | >25 | >25 |
| PC3 | Prostate cancer | 1.04 | >25 | >25 | >25 | >25 |
| LNCap | Prostate cancer | 0.97 | >25 | >25 | 2.44 | >25 |
| N87 | Gastric cancer | 0.14 | >25 | >25 | >25 | >25 |
| MKN45 | Gastric cancer | >25 | >25 | >25 | >25 | >25 |
| Panc-1 | Pancreatic cancer | 0.43 | | | | |
| MIAPACA | | 1.17 | | | | |
| MCF-7 | Breast cancer | 3.69 | >25 | >25 | >25 | >25 |
| HCT116 | Colon cancer | 5.64 | >50 | >50 | >50 | >50 |
| HT29 | Colon cancer | 31.1 | >50 | >50 | >50 | >50 |

Figure 1B:
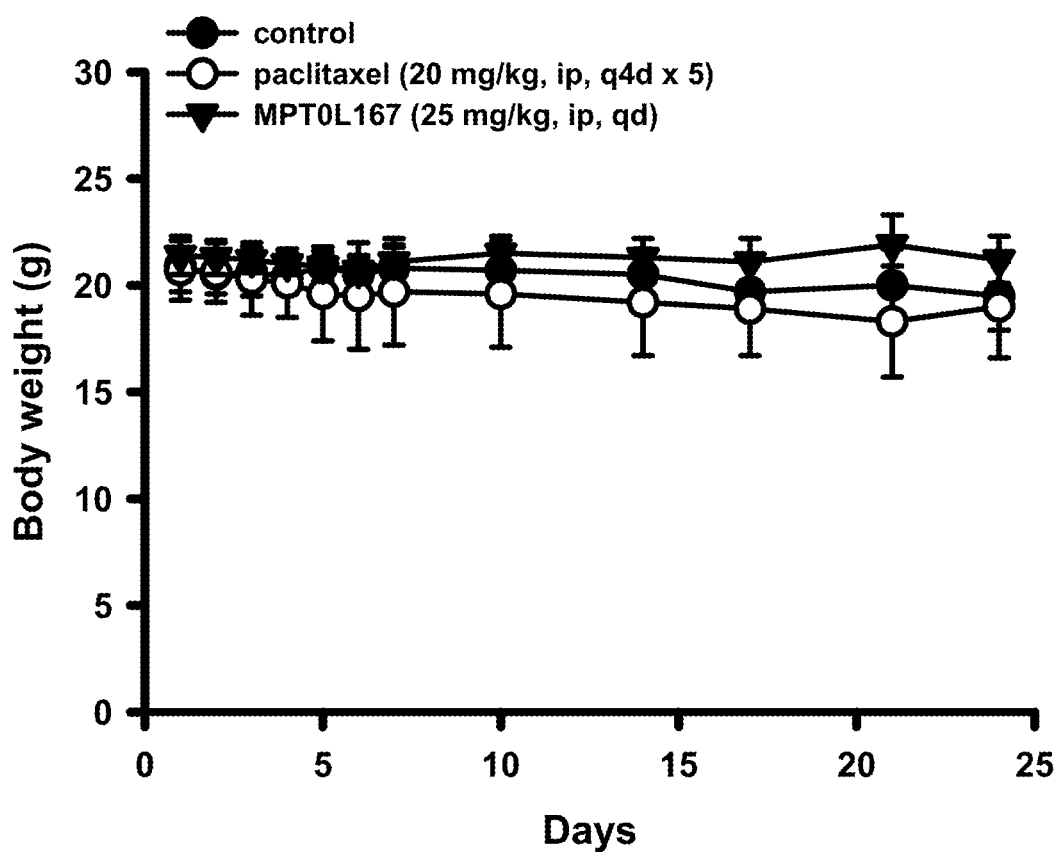

Anti-cancer Activity Evaluation of the Compounds of the Invention (MPT0L167 and MPT0L179) Against Human MDA-MB-231 Breast Cancer in MDA-MB-231 Xenograft Animal Model and Human Colorectal Cancer HCT116 Xenograft Model MPT0L167, MPT0L180 and MPT0L196 were each independently given orally (1.0% carboxyl methyl cellulose (CMC) and 0.5% Tween 80) to 8-week old female nude mice that had been implanted with human MDA-MB-231 breast cell line (1.0×10⁷ cells in suspension). This study utilized five groups of mice (n=7-8) bearing established human MDA-MB-231 breast adenocarcinoma with mean volumes of ~250 mm³. The tumor growth curve and animal body weight change for each treatment group are shown in the following figures, respectively. As shown in FIG. 1 (A), MPT0L167 significantly reduces tumor volume in breast cancer and has similar efficacy to paclitaxel (A). FIG. 1(B) shows that that the body weight of the mice administered with MPLOL167 did not exhibit significant change.

Figure 2A:
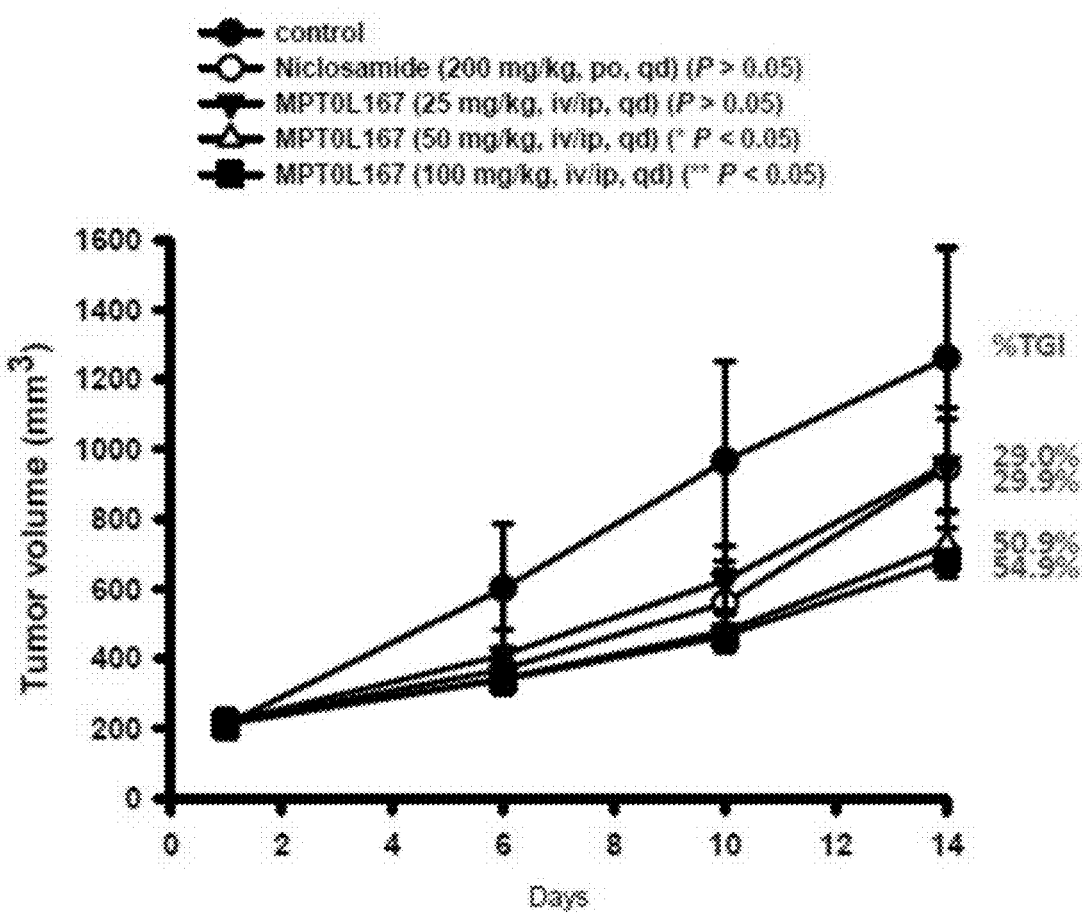
FIGS. 2(A) and (B) show the anticancer activity of MPT0L167 in human colorectal cancer HCT116 xenograft model. (A), MPT0L167 reduces tumor volume. (B), MPT0L167 does not significantly reduce body weight.
Figure 2B:
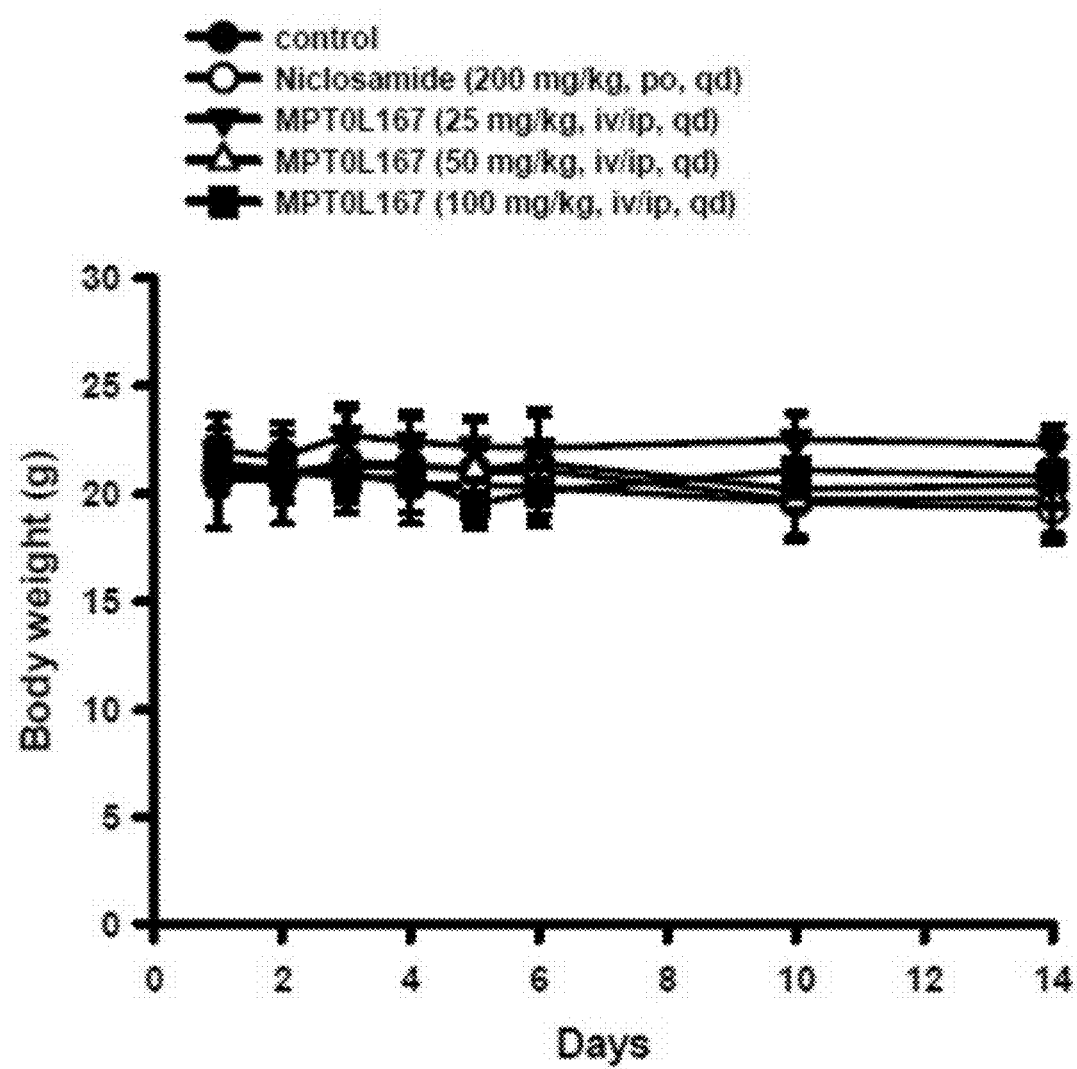

MPT0L167, MPT0L180 and MPT0L196 were each independently given orally (1.0% carboxyl methyl cellulose (CMC) and 0.5% Tween 80) to 8-week old female nude mice that had been implanted with human colorectal cancer HCT116 cell line (1.0×10⁷ cells in suspension). This study utilized five groups of mice (n=7-8) bearing established human HCT116 colorectal cancer with mean volumes of ~200 mm³. The tumor growth curve and animal body weight change for each treatment group are shown in the following figures, respectively. As shown in FIG. 2(A), MPT0L167 significantly reduces tumor volume in colorectal cancer and MPT0L167 in lower dose has similar efficacy to higher dose of niclosamide. FIG. 2(B) shows that the body weight of the mice administered with MPLOL167 did not exhibit significant change.

Pharmacokinetic Study (PK)

2 mg/kg of niclosamide (MPT0L166) and MPT0L167, MPT0L180 and MPT0L196 were each independently given to five rats by i.v. The blood samples were taken from the rats after 0.03 hour, 0.08 hour, 0.25 hour, 0.5 hour, 1 hour, 2 hours, 4 hours, 6 hour, 8 hours and 24 hours. LC-MS/MS was used to detect the concentration of MPT0L167 in blood. The PK results of MPT0L167 are shown in the table below. It is surprisingly found that MPT0L167 has longer half-life than MPT0L166 in vivo.

MPT0L167

| Sub | $T_{max}$ (hr) | $C_{max}$ (ng/mL) | $AUC_{0-t}$ (hr * ng/mL) | $AUC_{inf}$ (hr * ng/mL) | AUC % Extrap obs (%) | $MRT_{inf}$ (hr) | VZ obs (mL/kg) | CL obs (mL/hr/kg) | Half life (hr) | No Points Lambda z | Rsq |
|---|---|---|---|---|---|---|---|---|---|---|---|
| Mean | .03 | 3881 | 580 | 587 | 1.15 | 1.4 | 37344 | 3547 | 7.38 | — | |
| SD | 0.00 | 1056 | 131 | 134 | 0.436 | 0.34 | 14593 | 768 | 2.51 | — | |
| CV % | 0.00 | 27.2 | 22.6 | 22.8 | 37.9 | 24.3 | 39.1 | 21.7 | 34.1 | — | |

Figure 3A:
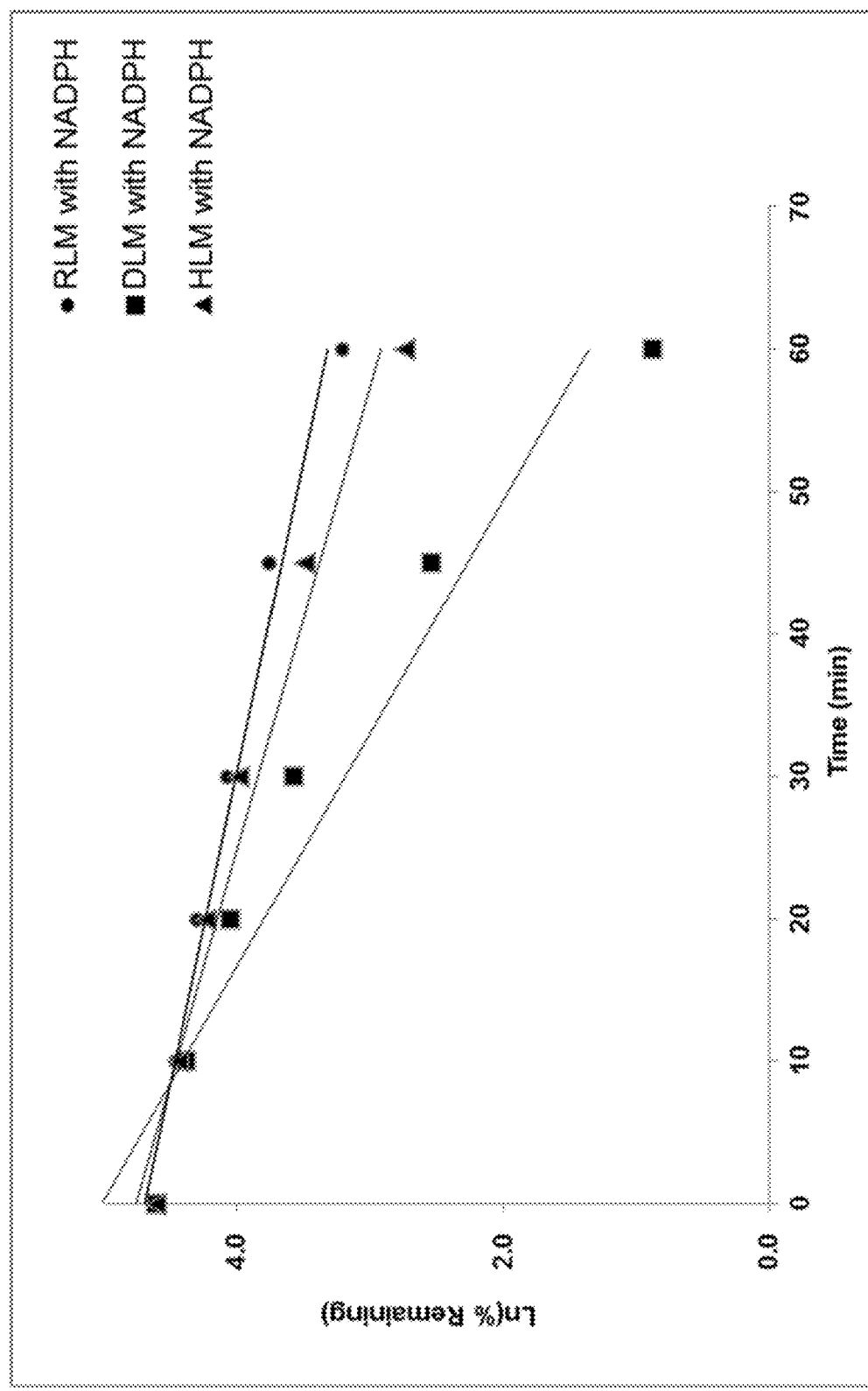
FIGS. 3(A) and (B) show the metabolic stability of MPT0L166 (A) and MPT0L167 (B).
Figure 3B:
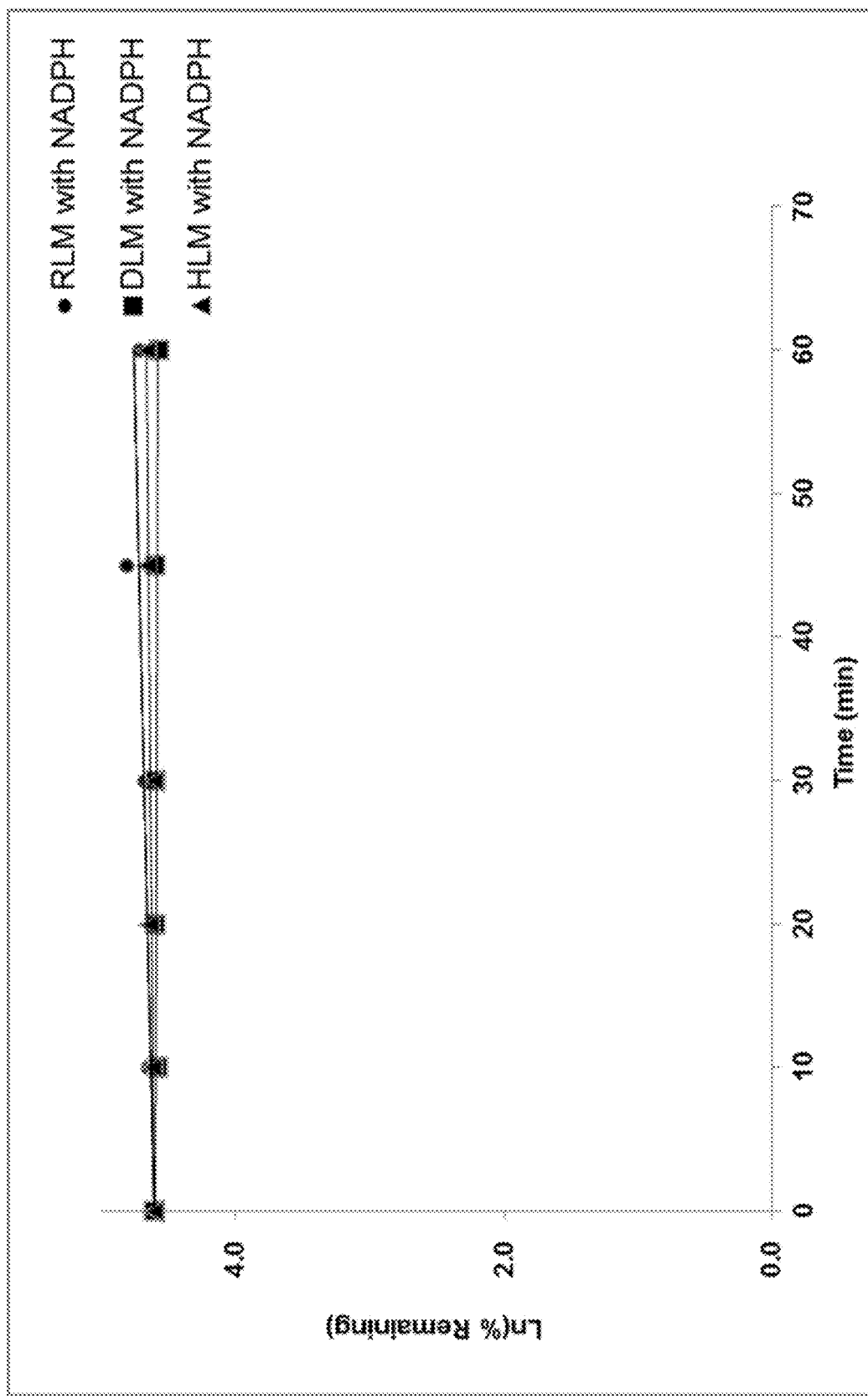

The metabolic stability of MPT0L166 and MPT0L167 in rat, dog and human liver microsomes is shown in FIGS. 3(A) and (B). The results show that the metabolism of MPT0L167 is more stable than MPT0L166.

Zika Animals Study

Figure 4A:
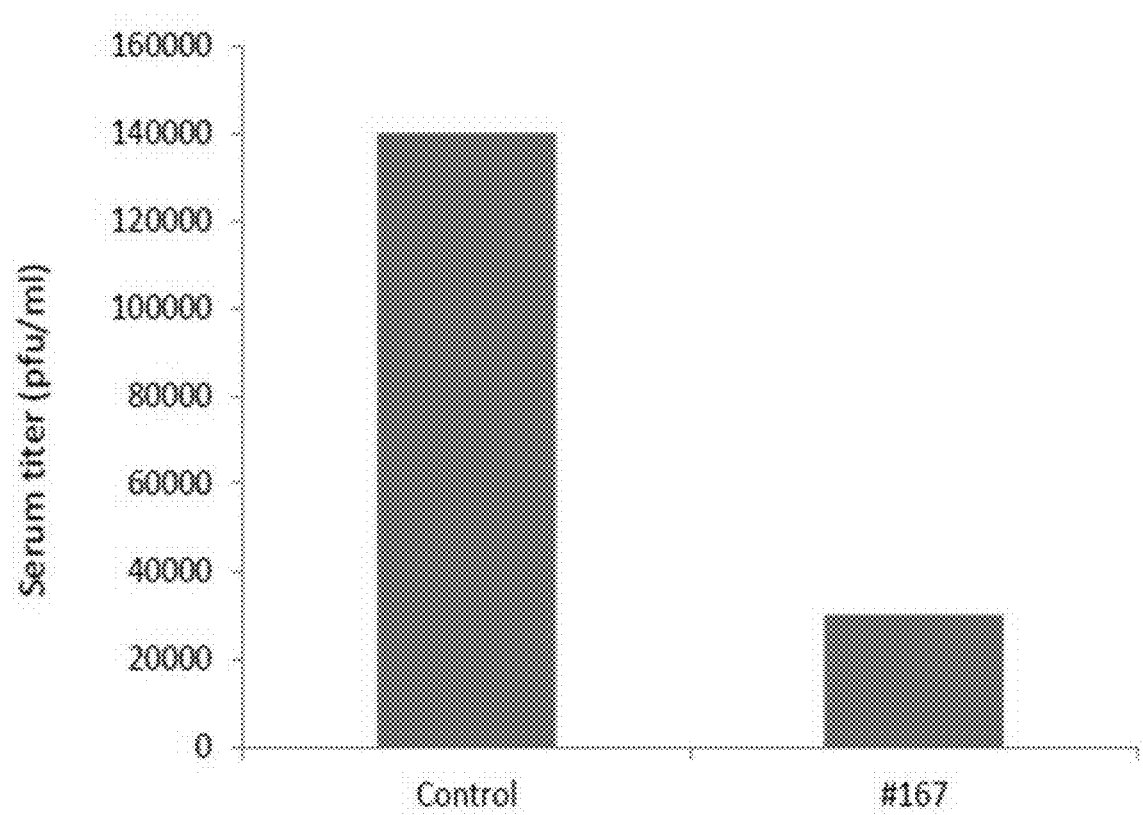
FIGS. 4(A) and (B) show the effect of MPT0L167 in inhibition of Zika virus infection in female mice (A) and MPT0L167 does not significant reduce body weight of the mice (B).
Figure 4B:
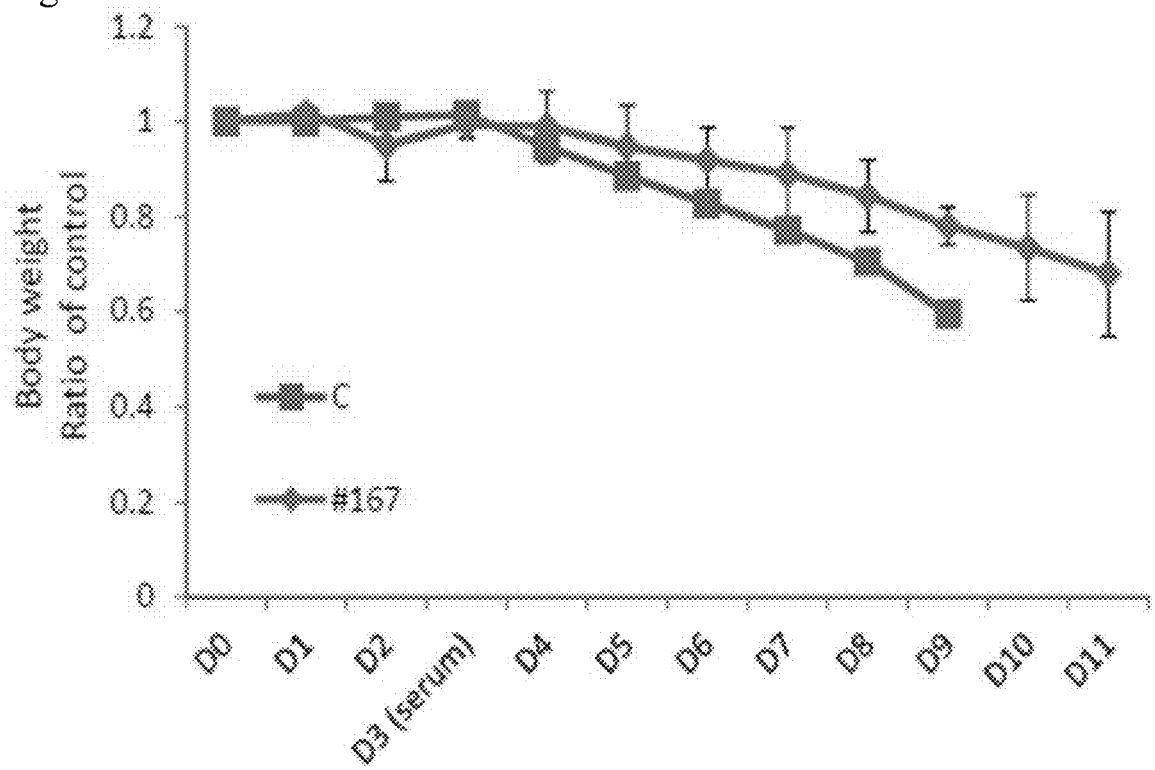

The Zika sensitive female mice: ROSA, STAT1⁻/⁻ strain was used. MPT0L167 was used to pre-treat the mice for one day. 4*10⁷ cells (U-87 MG human glioblastoma cell with infection with Zika virus (PRVABC59 strain)) were injection in mice. After infection, MPT0L167 was administered with 100 mg/kg to the mice by po,qd. The virus detection in serum at day 3. The concentration of virus in serum was detected by Viralplaque assays. FIG. 4 shows that MPT0L167 significantly inhibits Zika virua growth (A) in female mice, while the body weight of the mice is not significantly changed.

EXAMPLES

Example 1 Preparation of 5-Chloro-N-(2-chloro-4-nitro-phenyl)-2-(3,4,5-trihydroxy-6-hydroxymethyl-tetrahydro-pyran-2-yloxy)-benzamide (32)

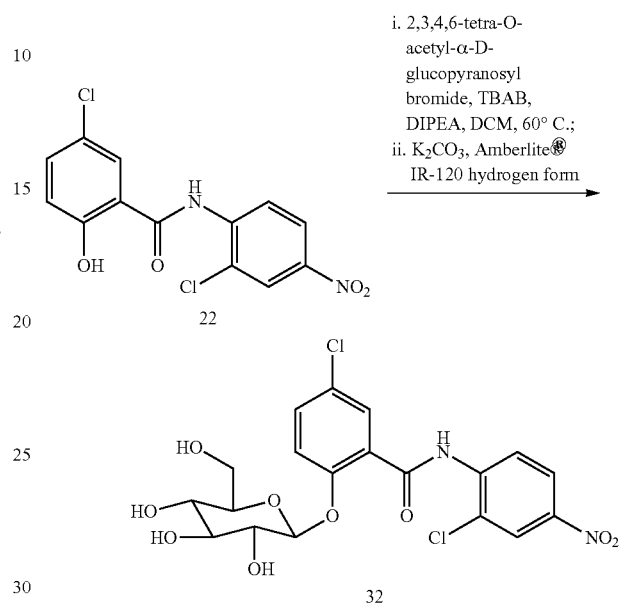

i. 2,3,4,6-tetra-O-acetyl-α-D-glucopyranosyl bromide, TBAB, DIPEA, DCM, 60° C.;
ii. K₂CO₃, Amberlite® IR-120 hydrogen form A solution of compound 22 (1.00 g, 3.06 mmol), 2,3,4, 6-tetra-O-acetyl-α-D-glucopyransoyl bromide (1.26 g, 3.06 mmol), tetra-n-butylammonium bromide (0.99 g, 3.07 mmol), diisoprpylethylamine (0.54 mL, 3.10 mmol), and anhydrous DCM (10 mL) was stirred at 60° C. The solution was purified by flash column chromatography on silica gel with EtOAc/n-Hexane to afford a white solid (0.81 g). The solid (0.81 g) was dissolved in MeOH (10 mL) and K₂CO₃ (0.46 g, 3.33 mmol) was added followed by stirring at room temperature. After reaction completed, the solution was neutralized with Amberlite® IR-120 (H⁺) resin to pH 7. The solid was filtered off and the filtrate was concentrated in vacuo, and the residue was purified by flash column chromatography on silica gel with DCM/MeOH to afford compound 32 (0.13 g, 9%, two steps) as a white solid: mp 212.6-213.2° C.; ¹H-NMR (300 MHz, MeOD) δ 3.35-3.54 (m, 3H), 3.66-3.73 (m, 2H), 3.90 (d, J=9.9 Hz, 1H), 5.18 (d, J=8.1 Hz, 1H), 7.47 (d, J=9.0 Hz, 1H), 7.58 (dd, J=2.7, 8.7 Hz, 1H), 8.07 (d, J=2.7 Hz, 1H), 8.24 (dd, J=2.7, 9.0 Hz, 1H), 8.41 (d, J=2.4 Hz, 1H), 8.66 (d, J=9.3 Hz, 1H). ¹³C-NMR (75 MHz, MeOD) δ 60.7, 69.6, 73.2, 76.5, 77.6, 102.1, 118.9, 123.1, 123.4, 124.7, 124.8, 126.9, 130.6, 133.9, 140.8, 143.4, 154.3, 162.1. HRMS (ESI) for $C_{19}H_{17}Cl_2N_2O_9$ (M-H$^+$) calcd 487.0311, found 487.0317; HPLC purity of 95.13% (retention time=25.27).

Example 2 Acetic acid 4-chloro-2-(2-chloro-4-nitro-phenylcarbamoyl)-phenoxymethyl ester (33)

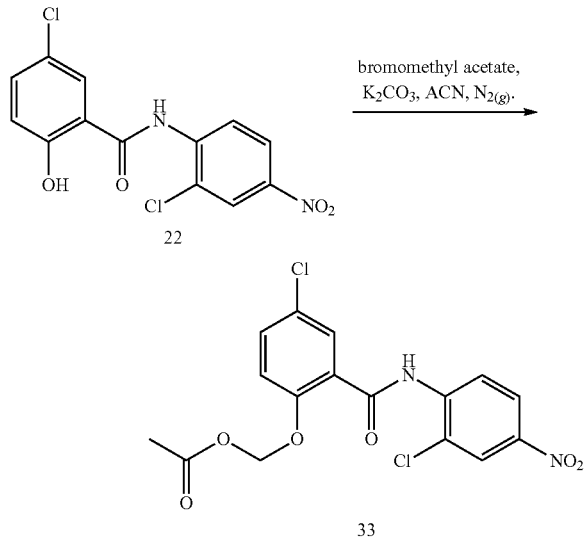

Bromomethyl acetate (0.14 mL, 1.43 mmol) was added to a suspension of compound 22 (0.40 g, 1.22 mmol) and K$_2$CO$_3$ (0.34 g, 2.46 mmol) in anhydrous ACN (4 mL). The mixture was stirred at room temperature. After the reaction had completed, the mixture was poured into water and then extracted with EtOAc. The combined organic layer was dried over MgSO$_4$, filtered and concentrated in vacuo to give a white solid. The solid was washed by EtOAc to afford compound 33 (0.49 g, 86%): mp 195.5-197.2° C.; $^1$H-NMR (300 MHz, CDCl$_3$) δ 2.16 (s, 3H), 5.99 (s, 2H), 7.23 (d, J=9.0 Hz, 1H), 7.52 (dd, J=2.7, 9.0 Hz, 1H), 8.20 (dd, J=2.4, 9.3 Hz, 1H), 8.27 (d, J=2.7 Hz, 1H), 8.34 (d, J=2.4 Hz, 1H), 8.90 (d, J=9.3 Hz, 1H); $^{13}$C-NMR (75 MHz, CDCl$_3$) δ 20.9, 84.9, 116.0, 120.9, 123.1, 123.2, 124.9, 129.4, 132.8, 134.1, 141.2, 143.2, 153.2, 161.9, 169.3; HRMS (ESI) for $C_{16}H_{11}Cl_2N_2O_6$ (M-H$^+$) calcd 396.9994, found 396.9999; HPLC purity of 100.00% (retention time=45.55).

Example 3 [1,4']Bipiperidinyl-1'-carboxylic acid 4-chloro-2-(2-chloro-4-nitro-phenylcarbamoyl)-phenyl ester (34)

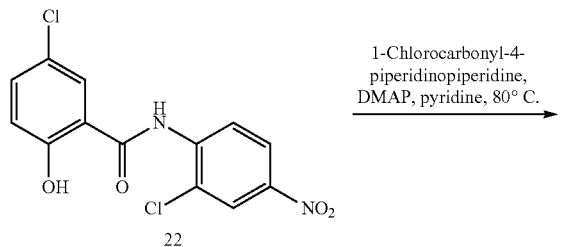

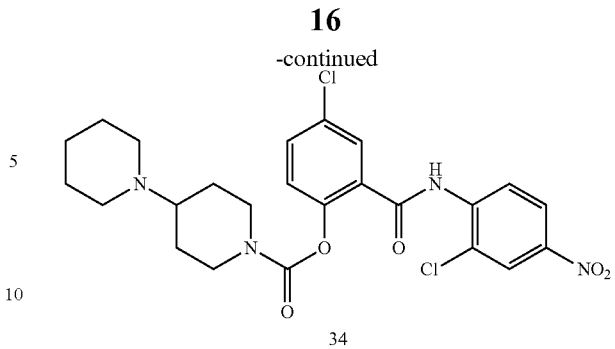

A solution 4-piperidinopiperidine (2.00 g, 11.88 mmol) in anhydrous DCM (50 mL) at 0° C. was added a solution of triphosgene (1.30 g, 4.38 mmol) in anhydrous DCM (10 mL). The mixture was stirred at room temperature overnight. The solid was removed by filtration and the filtrate was concentrated in vacuo to afford a white solid (1.35 g). The solid (1.35 g) was added to a suspension of niclosamide (22) (1.94 g, 5.93 mmol), DMAP (0.15 g, 1.23 mmol) in pyridine (15 mL) at room temperature, and stirred at 80° C. After the reaction had completed, the solution was cooled to room temperature and neutralized to pH 7. After filtration, the filtrate was concentrated in vacuo, and the residue was purified by flash column chromatography on silica gel with EtOAc/n-Hexane to afford compound 34 (0.87 g, 14%, two steps) as a pale white solid: mp 216.3-217.9° C.; $^1$H-NMR (300 MHz, CDCl$_3$) δ 1.54-1.84 (m, 8H), 2.02-2.17 (m, 4H), 2.72-3.06 (m, 8H), 4.28-4.40 (m, 2H), 5.30 (s, 1H), 7.14 (d, J=8.7 Hz, 1H), 7.53 (dd, J=2.4, 8.7 Hz, 1H), 7.82 (d, J=2.7 Hz, 1H), 8.20 (dd, J=2.4, 9.0 Hz, 1H), 8.33 (d, J=2.4 Hz, 1H), 8.50-8.80 (m, 2H); $^{13}$C-NMR (75 MHz, DMSO-d$_6$) δ 22.2, 23.2, 25.5, 43.0, 43.3, 48.9, 61.8, 123.1, 125.1, 125.5, 126.2, 127.4, 128.9, 129.5, 130.3, 131.8, 140.9, 144.5, 147.6, 152.1, 163.5; HRMS (ESI) for $C_{24}H_{25}Cl_2N_4O_5$ (M-H$^+$) calcd 519.1202, found 519.1206; HPLC purity of 100.00% (retention time=25.09).

Example 4 5-Chloro-2-hydroxy-N-(4-nitro-3-trifluoromethyl-phenyl)-benzamide

A suspension of compound 23a (0.50 g, 2.90 mmol) and 2-chloro-5-nitroaniline (0.60 g, 2.91 mmol) in p-xylene (10 mL) was heated to reflux under N$_2$. After heating to reflux, POCl$_3$ (0.11 mL, 1.18 mmol) was added and stirred under reflux for 4 h. The reaction mixture was cooled to room temperature and an equal volume of water added. The mixture was stirred for 30 min, and then was neutralized by aqueous NaOH to pH 7. The solution was extracted with DCM and the combined organic layer was purified by flash column chromatography on silica gel with EtOAc/n-Hexane to afford compound 25a (0.11 g, 11%) as a yellow solid: mp 172.4-174.0° C.; $^1$H-NMR (300 MHz, Acetone-d$_6$) δ 7.03 (d, J=9.0 HZ, 1H), 7.47 (dd, J=2.7, 8.7 Hz, 1H), 8.02 (d, J=2.4 Hz, 1H), 8.15 (d, J=9.0 Hz, 1H), 8.30 (dd, J=2.1, 9.0 Hz, 1H), 8.41 (d, J=2.1 Hz, 1H); $^{13}$C-NMR (75 MHz, Acetone-d$_6$) δ 117.7, 120.1, 120.2, 120.5, 121.3, 124.4, 124.6, 124.8, 124.9, 127.9, 128.8, 135.4, 143.4, 143.9, 159.6, 167.8; HRMS (ESI) for $C_{14}H_7ClF_3N_2O_4$ (M-H$^+$) calcd 340.9732, found 340.9721.

We claim:

1. A compound having the following Formula (I),

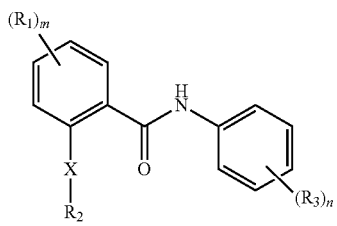

wherein
X is O;
m is an integer of 1 to 4;
n is an integer of 2 to 5;
$R_1$ is halogen, $NH_2$, $NO_2$, OH, $C_{1-10}$alkyl, $C_{2-10}$alkenyl, $C_{2-10}$alkynyl, $C_{1-10}$alkyloxy or $C_{1-10}$alkylthio;
$R_2$ is arabinopyranosyl, glucopyranosyl, galactopyranosyl, xylopyranosyl, arabinopyranosyl, ribopyranosyl, lyxopyranosyl, ribulopyranosyl, allopyranosyl, altropyranosyl, mannopyranosyl, idopyranosyl, arabinofuranosyl, glucofuranosyl, galactofuranosyl, xylofuranosyl, arabinofuranosyl, ribofuranosyl, lyxofuranosyl, ribulofuranosyl, allofuranosyl, altrofuranosyl, mannofuranosyl, idofuranosyl, C(O)pyridinyl, C(O)thienyl, —$C_{1-4}$alkyloxy-C(O)$C_{1-4}$alkyl, or —C(O)bipiperidinyl; or a tautomer, stereoisomer or enantiomer thereof, or a solvate or a pharmaceutically acceptable salt thereof; and
at least one of the $R_3$ groups is halogen and at least one is $NO_2$;
or a tautomer, stereoisomer or enantiomer thereof, or a solvate or a pharmaceutically acceptable salt thereof.

2. The compound of claim 1, wherein m is 1; and/or n is 2; or a tautomer, stereoisomer or enantiomer thereof, or a solvate or a pharmaceutically acceptable salt thereof.

3. The compound of claim 1, wherein $R_1$ is halogen or $C_{1-4}$alkyl; or a tautomer, stereoisomer or enantiomer thereof, or a solvate or a pharmaceutically acceptable salt thereof.

4. The compound of claim 1, wherein $R_1$ is Cl, or a tautomer, stereoisomer or enantiomer thereof, or a solvate or a pharmaceutically acceptable salt thereof.

5. The compound of claim 1, wherein $R_2$ is glucopyranosyl, 1,4'-bipiperidinylCOC(O)$CH_3$, or C(O)pyridinyl; or a tautomer, stereoisomer or enantiomer thereof, or a solvate or a pharmaceutically acceptable salt thereof.

6. The compound of claim 1, wherein $R_3$ is F, Cl, Br or $NO_2$; or a tautomer, stereoisomer or enantiomer thereof, or a solvate or a pharmaceutically acceptable salt thereof.

7. The compound of claim 1, wherein $R_3$ is Cl or $NO_2$; or a tautomer, stereoisomer or enantiomer thereof, or a solvate or a pharmaceutically acceptable salt thereof.

8. The compound of claim 1, which is selected from:

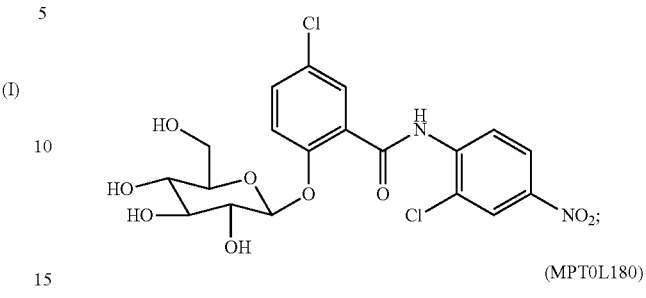
(MPT0L167)

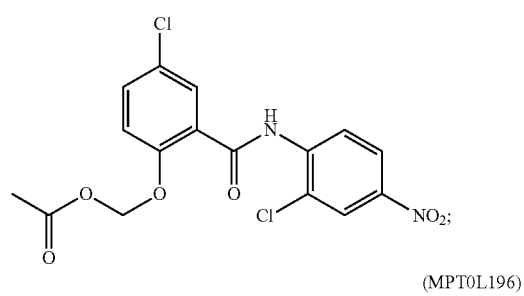
(MPT0L180)

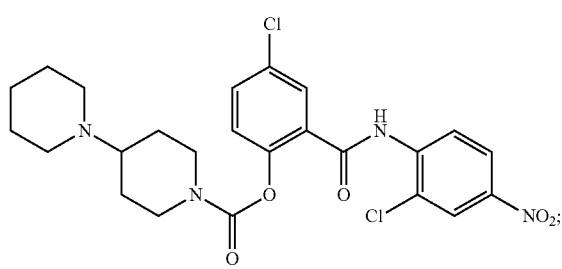
(MPT0L196)

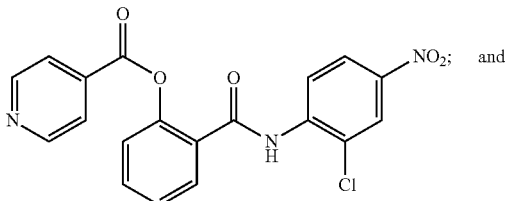
and

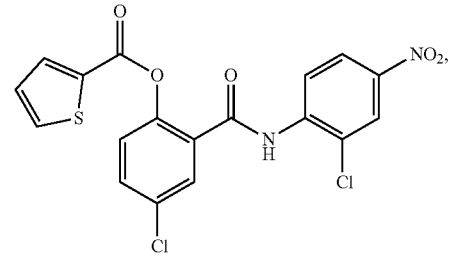

or a tautomer, stereoisomer or enantiomer thereof, or a solvate or a pharmaceutically acceptable salt thereof.

9. A pharmaceutical composition comprising a compound of Formula (I) of claim 1 or a tautomer, stereoisomer or enantiomer thereof, or a solvate or a pharmaceutically acceptable salt thereof.

10. A method for inhibiting tumor growth in a subject, comprising administering to the subject a therapeutically effective amount of the compound of Formula (I) of claim 1.

11. A method for treating a cancer selected from prostate, gastric, pancreatic, breast, colon, and colorectal cancer, comprising administering to a subject an effective amount of the compound of Formula (I) of claim 1.

12. The method of claim 11, which comprises further administering a second therapeutic agent.

13. The method of claim 12, wherein the compound of claim 1 and the second therapeutic agent is administered substantially simultaneously or concurrently.

* * * * *